United States Patent
Briche (10) Patent No.: US 11,680,236 B2
(45) Date of Patent: Jun. 20, 2023

(54) THIN, UNIFORM, STACKABLE PETRI DISH

(71) Applicant: CORNING INCORPORATED, Corning, NY (US)

(72) Inventor: Christophe Roland René Briche, Ferfay (FR)

(73) Assignee: CORNING INCORPORATED, Corning, NY (US)

( * ) Notice: Subject to any disclaimer, the term of this patent is extended or adjusted under 35 U.S.C. 154(b) by 98 days.

(21) Appl. No.: 16/766,848

(22) PCT Filed: Nov. 20, 2018

(86) PCT No.: PCT/US2018/062087
§ 371 (c)(1),
(2) Date: May 26, 2020

(87) PCT Pub. No.: WO2019/108445
PCT Pub. Date: Jun. 6, 2019

(65) Prior Publication Data
US 2020/0318047 A1    Oct. 8, 2020

(30) Foreign Application Priority Data
Nov. 30, 2017  (EP) .................................... 17306672

(51) Int. Cl.
*C12M 1/22* (2006.01)
*C12M 1/00* (2006.01)
*C12M 3/00* (2006.01)

(52) U.S. Cl.
CPC ............ *C12M 23/10* (2013.01); *C12M 23/38* (2013.01); *C12M 23/44* (2013.01); *C12M 29/20* (2013.01)

(58) Field of Classification Search
None
See application file for complete search history.

(56) References Cited

U.S. PATENT DOCUMENTS

| 2,533,088 A | 12/1950 | Brewer et al. |
| 2,533,089 A | 12/1950 | Brewer et al. |

(Continued)

FOREIGN PATENT DOCUMENTS

| CN | 101541428 A | 9/2009 |
| CN | 201817486 U | 5/2011 |

(Continued)

OTHER PUBLICATIONS

Extended European Search Report and Search Opinion; 17306672.1; dated May 18, 2018; 11 pages; European Patent Office.

(Continued)

*Primary Examiner* — William H. Beisner
(74) *Attorney, Agent, or Firm* — F. Brock Riggs (57) ABSTRACT

A Petri dish (100) base (300) and lid (200) each having a substantially circular, substantially flat region from which sidewalls extend perpendicular to the flat region (312) forming a corner (326), (230). The base may have a base stacking ring (325) extending from the base (300) at the corner (326), and an internal channel (330) around the inside of the base (300) at the corner (326). The base (300) may have a uniform cross-sectional thickness (350) and may also have vents (322) in the base stacking ring (325). The lid (200) may have a uniform cross-sectional thickness (250). The lid (200) may have a lid stacking ring (225) at the corner (230), which forms a groove (240) in the interior (212) of the lid (200) at the corner (230). The lid may also have ribs (295) and vents (222) to enable multiple dishes to be stacked without forming a vacuum.

12 Claims, 10 Drawing Sheets

(56) References Cited

U.S. PATENT DOCUMENTS

| | | | |
|---|---|---|---|
| 2,694,033 | A | 11/1954 | Fletcher |
| 2,971,892 | A | 2/1961 | Carski |
| 3,055,808 | A | 9/1962 | Henderson |
| 3,158,553 | A | 11/1964 | Carski |
| 3,203,870 | A | 8/1965 | Philip |
| 3,499,825 | A | 3/1970 | Falcone et al. |
| 3,649,463 | A | 3/1972 | Buterbaugh |
| 3,960,658 | A | 6/1976 | Avakian et al. |
| 4,160,700 | A | 7/1979 | Boomus |
| 4,255,522 | A | 3/1981 | Fusenig |
| D272,185 | S | 1/1984 | Schlesinger |
| D295,319 | S | 4/1988 | Franchere et al. |
| 4,743,556 | A | 5/1988 | Ervin |
| 4,966,744 | A * | 10/1990 | Sorensen ............ B29C 45/0025 425/577 |
| 4,981,802 | A | 1/1991 | Wylie et al. |
| 5,021,351 | A | 6/1991 | Ervin |
| 5,366,893 | A | 11/1994 | Stevens et al. |
| D425,624 | S | 5/2000 | Choi |
| 6,540,078 | B1 * | 4/2003 | Homent ............... B65D 43/162 220/839 |
| 6,969,607 | B2 | 11/2005 | Minton |
| D563,560 | S | 3/2008 | Copeland |
| D578,654 | S | 10/2008 | Chianea |
| 7,452,711 | B2 | 11/2008 | Daykin |
| 2003/0186429 | A1 | 10/2003 | Goff et al. |
| 2005/0003525 | A1 | 1/2005 | Hsu |
| 2005/0089997 | A1 | 4/2005 | Minton |
| 2012/0125936 | A1 * | 5/2012 | Byers .................... C12M 29/20 220/367.1 |
| 2013/0011566 | A1 | 1/2013 | Colin et al. |
| 2013/0084633 | A1 | 4/2013 | Shin et al. |
| 2017/0166851 | A1 | 6/2017 | Zheng et al. |

FOREIGN PATENT DOCUMENTS

| | | |
|---|---|---|
| CN | 202688322 U | 1/2013 |
| CN | 202766542 U | 3/2013 |
| CN | 103013819 A | 4/2013 |
| CN | 203048938 U | 7/2013 |
| CN | 204325362 U | 5/2015 |
| CN | 105802842 A | 7/2016 |
| CN | 106479888 A | 3/2017 |
| DE | 2408109 A1 | 8/1975 |
| EP | 0171174 A2 | 2/1986 |
| EP | 0401660 A1 | 12/1990 |
| EP | 0952211 A1 | 10/1999 |
| EP | 1035201 A1 | 9/2000 |
| IL | 29649 A | 12/1971 |
| JP | 11-290848 | 10/1999 |
| JP | 2001-112464 A | 4/2001 |
| JP | 2003-047459 A | 2/2003 |
| JP | 2003047459 A * | 2/2003 ............ C12M 23/10 |
| JP | 2003-145813 A | 5/2003 |
| JP | 2003-193337 A | 7/2003 |
| JP | 2004-337057 A | 12/2004 |
| JP | 2004-350504 A | 12/2004 |
| JP | 2005-310888 A | 11/2005 |
| JP | 2005-312317 A | 11/2005 |
| JP | 2006-129713 A | 5/2006 |
| JP | 2007-049968 A | 3/2007 |
| JP | 4146626 B2 | 9/2008 |
| JP | 2008-278772 A | 11/2008 |
| JP | 2010-004951 A | 1/2010 |
| JP | 2010-080268 A | 4/2010 |
| JP | 2011-211990 A | 10/2011 |
| JP | 2012-075410 A | 4/2012 |
| JP | 2015-047128 A | 3/2015 |
| JP | 2015-226532 A | 12/2015 |
| JP | 6032345 B2 | 11/2016 |
| JP | 2017-063618 A | 4/2017 |
| KR | 10-0836827 B1 | 6/2008 |
| KR | 10-2016-0036681 A | 4/2016 |
| KR | 10-2017-0051908 A | 5/2017 |
| TW | 538906 | 6/2003 |
| WO | 2004/072219 A1 | 8/2004 |
| WO | 2007/149525 A2 | 12/2007 |
| WO | 2009/033263 A1 | 3/2009 |
| WO | 2009/114138 A2 | 9/2009 |
| WO | 2011/160911 A1 | 12/2011 |
| WO | 2014/127774 A1 | 8/2014 |
| WO | 2016/074614 A1 | 5/2016 |

OTHER PUBLICATIONS

International Search Report and Written Opinion of the International Searching Authority; PCT/US2018/062087; dated Jan. 29, 2019; 12 Pages; European Patent Office.

Chinese Patent Application No. 201880077844.2, Office Action dated Feb. 14, 2023, 5 pages (English Translation only), Chinese Patent Office.

* cited by examiner

THIN, UNIFORM, STACKABLE PETRI DISH

CROSS REFERENCE TO RELATED APPLICATION

This is a national stage application under 35 U.S.C. § 371 of International Application No. PCT/US2018/062087, filed Nov. 20, 2018, which claims the benefit of priority under 35 U.S.C. § 119 of European Patent Application Ser. No. 17306672.1 filed on Nov. 30, 2017, the contents of which are relied upon and incorporated herein by reference in their entirety.

FIELD

The present disclosure generally relates to laboratory consumables, and more specifically to stackable Petri dishes having a uniform cross section.

BACKGROUND

Petri dishes are shallow glass or plastic lidded containers used to culture cells. Petri dishes are often used to make agar plates for microbiological studies where a base unit is partially filled with liquid containing agar and additional optional components such as nutrients, blood, salts, carbohydrates, indicators, amino acids or antibiotics. Once the agar cools and solidifies, a Petri dish is inoculated ("plated") with a microbe-laden sample. During use or storage, Petri dishes may be stacked.

Conventionally, Petri dishes are manufactured via injection molding using crystal polystyrene. For such a process, the cost of the raw materials accounts for as much as 50% of the cost of the product. It is therefore desirable to reduce the volume of raw material used to form Petri dishes while maintaining their function, including their stackability.

SUMMARY

Disclosed herein is a Petri dish base having a substantially circular, substantially flat base region from which a base sidewall extends perpendicular to the flat base region forming a corner, which may have a base stacking ring extending from the outside of the base at the corner, and which also defines an internal channel around the inside of the base at the corner. The base may have a uniform cross-sectional thickness. The base may also have vents in the base stacking ring. The Petri dish may also have a lid which may also have a uniform cross-sectional lid thickness. The lid may have a flat circular region and downwardly extending sidewalls forming a corner. The lid may have a lid stacking ring at the corner, which forms a groove in the interior of the lid at the corner. The lid may also have ribs and vents to enable multiple dishes to be stacked.

The disclosure provides, in an aspect (1) a dish having a polymeric base having a circular dish region, a corner, and an upwardly extending sidewall; a channel in an interior surface of the base at the corner; a base stacking ring in an exterior surface of the base at the corner; wherein each of the circular base portion, the upwardly extending sidewall and the corner have a thickness; and wherein the thicknesses of the circular base portion, the upwardly extending sidewall and the corner are within 30% of each other.

The disclosure provides, in an aspect (2) The dish of aspect 1 further comprising at least three base vents in the base stacking ring. In another aspect (3), the disclosure provides the dish of aspect (2) comprising at least 4 base vents in the base stacking ring. In another aspect (4), the disclosure provides the dish of aspect (2) wherein the base vents are arranged equidistant from each other. In another aspect (5), the disclosure provides the dish of any one of the preceding aspects wherein the base stacking ring is interrupted by a gate.

In an additional aspect (6) the disclosure provides the dish of any one of the preceding aspects and further including a polymeric lid. In an aspect (7), the disclosure provides the dish of aspect 6, wherein the lid comprises a circular lid portion, a corner, and a downwardly extending sidewall; a groove in an interior surface of the lid at the corner; a lid stacking ring in an exterior surface of the lid at the corner; wherein each of the circular lid portion, the downwardly extending sidewall and the corner have a thickness; and wherein the thickness of the circular lid portion, the downwardly extending sidewall and the corner are within 30% of each other. In an aspect (8), the disclosure provides the dish of aspect 7, wherein the lid further comprises at least 3 ribs extending downwardly from the interior surface of the lid, at the connection between the circular lid portion and the downwardly extending lid wall. In an aspect (9) the disclosure provides the dish of aspect 8 wherein the ribs are triangular, or are equidistant from each other. In an aspect (10), the disclosure provides the dish of any one of aspects 6-9 wherein the lid further comprising at least three vents. In an aspect (11), the disclosure provides the dish of aspect 10, wherein the vents are equidistant from each other or co-located with each other or wherein the lid stacking ring is interrupted by a gate.

In an additional aspect (12) the disclosure provides a dish and lid of any of the above aspects, wherein, when stacked one on top of the other, the base stacking ring of the top dish fits within the lid stacking ring of the other dish.

Additional features and advantages of the present disclosure will be set forth in the detailed description which follows, and in part will be apparent to those skilled in the art after reading and understanding the detailed description or recognized by practicing the embodiments described herein, including the detailed description which follows, the claims, and the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF SEVERAL VIEWS OF THE DRAWINGS

The following is a description of the figures in the accompanying drawings. The figures are not necessarily to scale, and certain features and certain views of the figures may be shown exaggerated in scale or in schematic in the interest of clarity or conciseness.

FIGS. 2A, 2B and 2C illustrate schematic perspective views of an embodiment of a lid according to an embodiment of the present disclosure.

FIGS. 3A, 3B, 3C and 3D illustrate views of a lid according to an embodiment of the present disclosure.

FIGS. 4A-4E illustrate views of a lid according to another embodiment of the present disclosure.

FIGS. 5A-5F illustrate views of a Petri dish or base according to an embodiment of the present disclosure.

FIGS. 6A-6D illustrate views of a Petri dish or base according to an embodiment of the present disclosure.

FIGS. 7A and 7B illustrate stacked Petri dishes with lids.

The foregoing summary, as well as the following detailed description, will be better understood when read in conjunction with the figures. It should be understood that the claims are not limited to the arrangements and instrumentality shown in the figures. Furthermore, the appearance shown in the figures is one of many ornamental appearances that can be employed to achieve the stated functions of the apparatus.

DETAILED DESCRIPTION

In the following detailed description, numerous specific details are set forth in order to provide a thorough understanding of the present invention. However, it will be clear to one skilled in the art when the present invention can be practiced without some or all of these specific details. In other instances, well-known features or processes may not be described in detail so as not to unnecessarily obscure the invention. In addition, like or identical reference numerals may be used to identify common or similar elements.

Figure 1A:
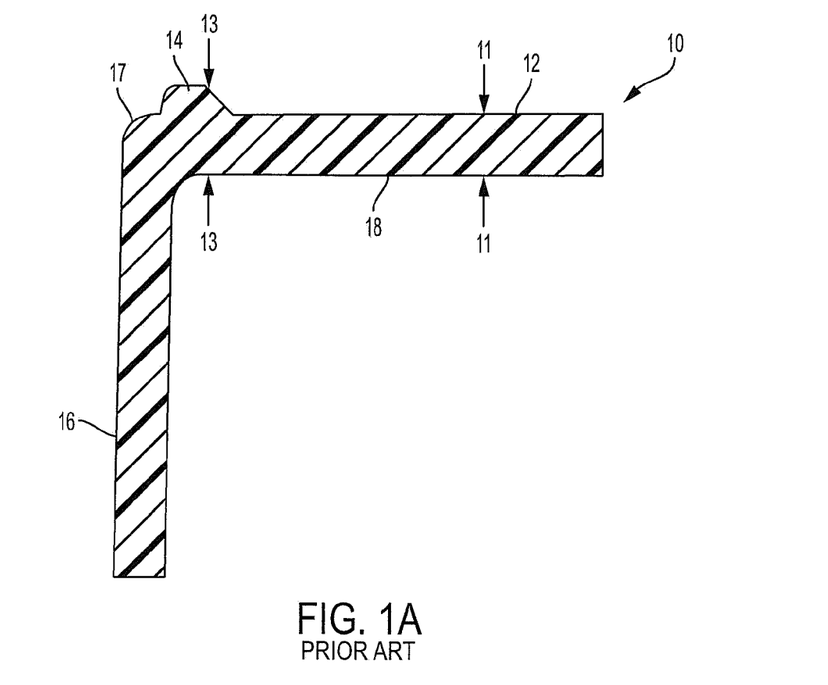
FIGS. 1A and 1B illustrate schematic cross-sectional views of a prior art Petri dish (FIG. 1B) and lid (FIG. 1A).
Figure 1B:
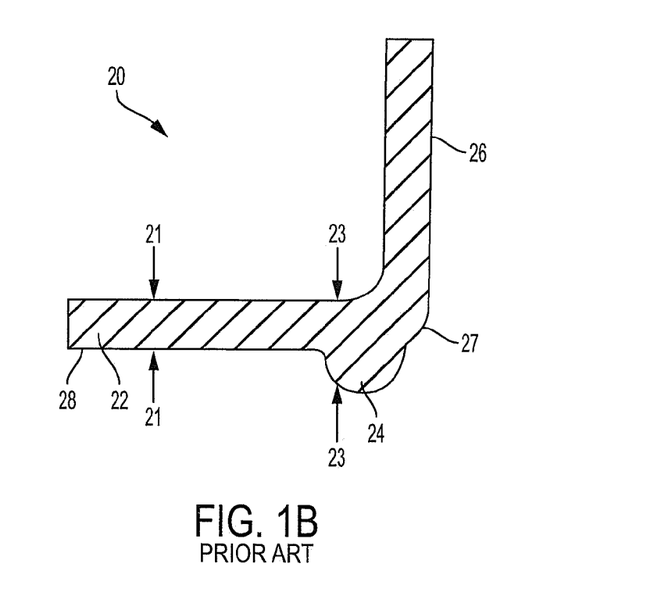

A partial cross-sectional illustration of a prior art Petri dish (lid and base) is shown in FIGS. 1A and 1B. Prior art lid 10 includes a substantially planar lid top wall 12 and a peripheral downwardly-extending lid sidewall 16. Prior art base 20 includes a substantially planar base bottom wall 22 and a peripheral upwardly-extending base sidewall 26.

In the illustration of the prior art lid shown in FIG. 1A, extending from an upper edge of the lid top wall 12 is a peripheral lid ridge 14 adapted to engage with the bottom surface of an overstacked prior art base 20. The peripheral lid ridge 14 is an annular ridge 14 interior to the corner 17 of the lid 10 on the top surface of the of the lid top wall 12. In cross section, as shown in FIG. 1A, the peripheral lid ridge 14 is a bump; a local increase in the thickness of the cross section of the lid 10 at the peripheral lid ridge 13 compared to the lid top wall thickness 11.

In the prior art base 20 shown in FIG. 1B, extending from a lower edge 28 of the base bottom wall 22 is a peripheral base ridge 24. Peripheral base ridge 24 is an annular ridge interior to the corner 27 of the base 20. Peripheral base ridge 24 is adapted to contact a support surface such as a table, or, if stacked, to engage with peripheral lid ridge 14 of the top wall 12 of an underlying prior art lid 10. In cross section, as shown in FIG. 1B, the peripheral base ridge 24 is also a bump; a local increase in the thickness of the cross section of the base 20 at the peripheral base ridge 23 compared to the base bottom wall thickness 21.

Though peripheral ridges 14, 24 facilitate stacking of the prior art Petri dish according to FIGS. 1A and 1B, the ridge design requires additional raw material to provide the thickened features. This results in a prior art Petri dish having a variable wall thickness, where the walls of both the prior art lid 10 and the prior art base 20 are locally thicker in the region of the peripheral ridges 14, 24. Such prior art Petri dishes contain about 14.3 g polystyrene per Petri dish (lid and base combined).

These local differences in thickness of both the base and the lid create challenges when manufacturing these dishes by injection molding. The process of injection molding is, stated simply, a process that includes introducing liquid raw material into a mold, allowing the raw material to flow until it is present in all areas of the mold, allowing the raw material to cool and harden, and removing the molded article from the mold. Raw material flows into a mold that defines a uniform thickness of article at a uniform speed. However, when a mold has thicker regions, such as those shown at 13 (compared to 11) in FIG. 1A or 23 (compared to 21) in FIG. 1B, liquid raw material flows more quickly into the thicker regions. When there is a localized thick region, the flow of resin may be discontinuous. For example, the raw material may fill the thick region before the wall is filled with raw material, causing a bubble or bubbles to form in the molded article. Petri dishes having bubbles formed in the molded article are defective. Not only does this bubble formation lead to a molded article that is not acceptable, the formation of a bubble damages the mold itself. Over time, molds that have gone through multiple cycles of molding articles that have air pockets will create petri dishes having reduced polish on the surface of the molded article.

At the same time, stacking rings on the lid and base of petri dishes are useful features which improve the stackability of dishes. Petri dishes are stacked for shipping and in use. Tall stacks of twenty or more Petri dishes are not uncommon. And, especially when automated equipment is in use, it is important to be able to slide one Petri dish away from a stack of Petri dishes without disrupting the stack of Petri dishes. So peripheral ridges or other structures useful to keep a stack of Petri dishes stacked must not introduce so much restriction of movement that a single dish in a stack of dishes cannot be moved away from the stack without disrupting the stack. Lids should be removable, manually or using automation equipment. And, the interior surface of the base of the Petri dish should be flat. In addition, it is important that the Petri dishes have features that allow them to be stacked in tall stacks that are stable and straight. That is, when stacked in tall stacks, the Petri dishes, in embodiments, do not "lean" to one side or another.

In embodiments, the Petri dish disclosed herein has peripheral lid and base stacking rings. However, these rings do not introduce localized thickening of the material at the area of the lid and base stacking rings. Instead, in embodiments, the Petri dishes disclosed herein have a base with a base wall, sidewall and base stacking ring each having a similar cross-sectional thickness. The Petri dishes disclosed herein also have a lid with a lid wall, lid sidewall and a lid stacking ring each having a uniform cross-sectional thickness. In embodiments, these structures result in molded articles that retain features that are important for stacking and use of the articles, have fewer manufacturing defects, and use less material that prior art articles. By reducing the wall thickness at the region of the peripheral ridges, 15-20% less material may be required to make each Petri dish 100.

Figure 2A:
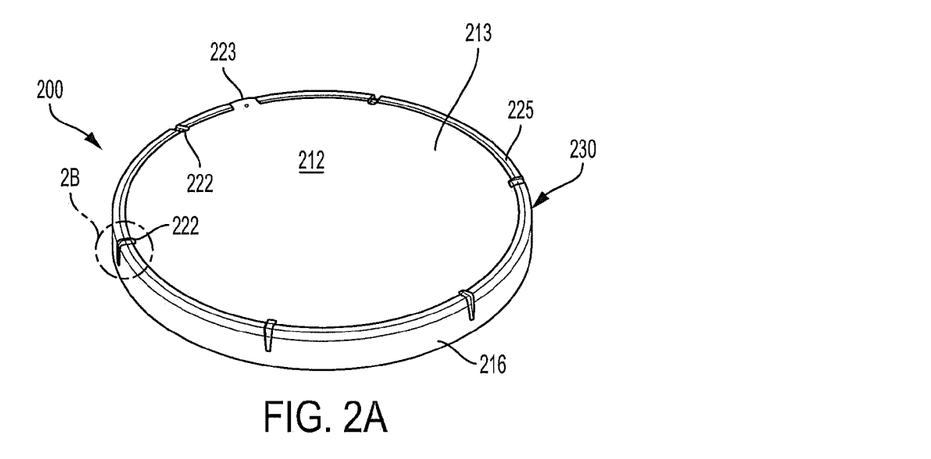
FIG. 2A is a perspective view of the exterior of the lid.
Figures 2B, 2C:
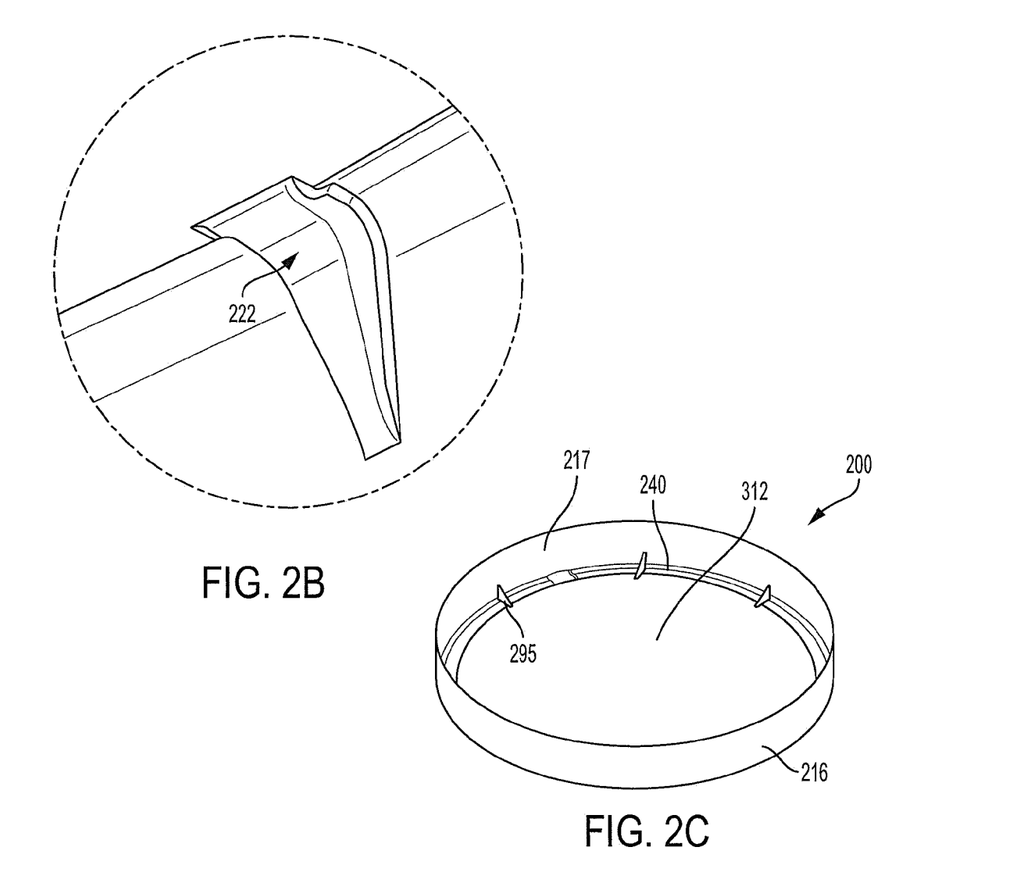
FIG. 2B is a blown-up view of region 2B shown in FIG. 2A.
FIG. 2C is a perspective view of the interior of the lid.

FIGS. 2A, 2B and 2C illustrate schematic perspective views of an embodiment of a lid according to an embodiment of the present disclosure. FIG. 2A is a perspective view of the exterior of the lid. FIG. 2B is a blown-up view of region 2B shown in FIG. 2A. FIG. 2C is a perspective view of the interior of the lid.

FIG. 2A is a perspective view of the exterior of a lid, according to embodiments of the present disclosure. FIG. 2A illustrates a lid 200 having a circular flat lid region 212 having an exterior lid top surface 213, a downwardly extending lid sidewall 216, and a corner 230 at the intersection of the lid top 212 and the lid sidewall 216. The corner 230 includes lid stacking ring 225. In embodiments, lid stacking ring 225, seen from the top, is a raised ring of material at the corner 230 of the lid 200. In embodiments, the lid is made from polymeric material.

Optionally, in embodiments, the lid may also have vents 222 FIG. 2B is a blown-up view of region 2B shown in FIG. 2A, showing an embodiment of a vent 222. In embodiments, one or more vents 222 are present in the corner 230 of the lid 200. In embodiments, the vent 222 is an indentation in the corner of the lid. The vent 222 functions to create a pathway for air to flow between a lid 200 and a base 300 of the next stacked Petri dish. The vents 222 allow air to pass between the lid 200 and the base 300. It is important to exchange external air with the air inside the Petri dish 100. Bacteria, or other cells growing inside a Petri dish needs oxygen to grow. In embodiments the lid vents 222 are arranged equidistant from each other around the lid stacking ring 225.

Often, when Petri dishes are stacked, for storage, shipment or in use, a vacuum forms between a lid and a base of the next stacked Petri dish. This vacuum may be created due to cooling air between parts, static properties of the material of the parts, pressure on the parts because of the weight of stacked parts, or due to the geometry of the parts. The vacuum causes difficult in maneuvering stacked parts. The parts "stick" together. This makes it difficult remove one dish from a stack of dishes, makes it difficult to manipulate parts in lid-base pairs, and makes robotic manipulation of the dishes difficult. Sticky parts result in breakage, separation of lids from plates, contamination, and may require maintenance of robotic equipment. For example, if a lid sticks to a base of an adjacent stacked Petri dish, when a user or a robot seeks to remove a single Petri dish from a stack of Petri dishes, the user may lift a lid stuck to an adjacent base instead of a lid sitting on top of a base. This would remove the lid from the mated dish. Opening the dish, removing the lid from the dish, creates an opportunity for contamination inside the dish. Therefore, there is a need for features which function to create air flow between the top 212 of a lid 200 and the bottom surface of an adjacent stacked dish (see, for example, 312 at FIG. 5D or FIG. 6B). Vent 222 is such a feature. Additional vacuum-breaking or vent features will be discussed in later figures.

FIG. 2C is a perspective view of the interior of the lid. FIG. 2C illustrates the interior top surface 312 of the lid and the sidewall 216 having an interior surface 217. Also illustrated in FIG. 2C is an optional rib 295. In embodiments, rib 295 is a triangular feature that extends between the interior top surfaced 312 of the lid 200 and the sidewall 216 of the lid 200. When the lid 200 having ribs 295 is placed on a base 300, the lid 200 aligns with respect to the base 300. Because the ribs 295 are triangular in shape, the lid 200 settles against the base 300 in a way that ensures that the lid 200 and the base 300 are coaxial. That is, the center of the lid 200 aligns with the center of the base 300 (see, for example, FIG. 7A and FIG. 7B). In embodiments, lid 200 may have three or more ribs. For example, lid may have 4, 5, 6 7, 8 or more ribs 295. In embodiments the ribs 295 are spaced equally around the corner 230 of the lid 200. That is, in embodiments the ribs 295 are arranged equidistant from each other around the lid stacking ring 225.

Figure 4A:
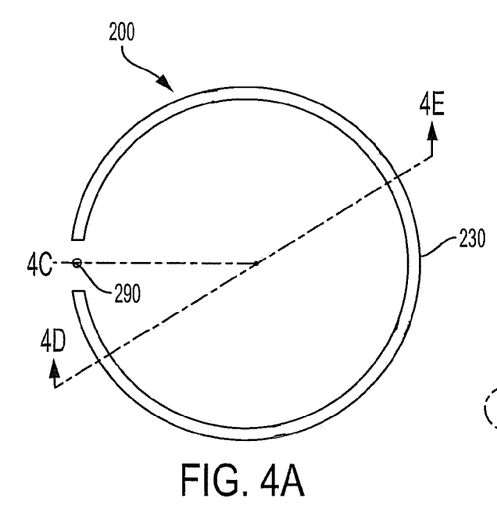
FIG. 4A is a top-down view of the external surface of a lid, according to embodiments.
Figure 4B:
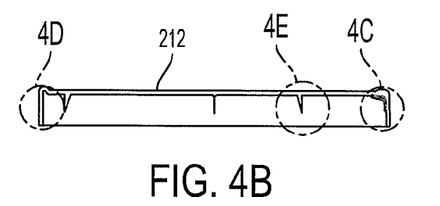
FIG. 4B is a cross-sectional view of a lid, taken at line 4B-C of FIG. 4A.
Figure 4C:
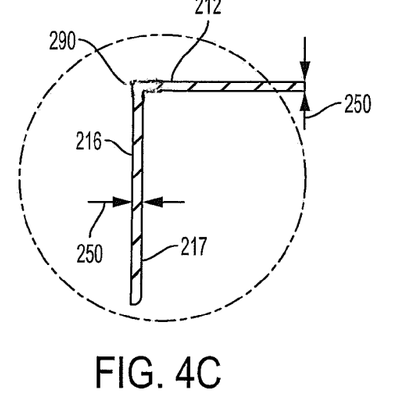
FIG. 4C is a blown-up view of the region shown as 4C in the cross-sectional view of FIG. 4B.
Figure 4D:
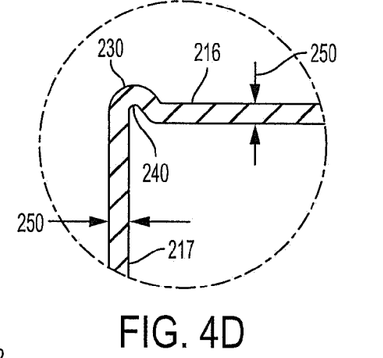
FIG. 4D is a blown-up view of the regions shown as 4D in the cross-sectional view of FIG. 4B.
Figure 4E:
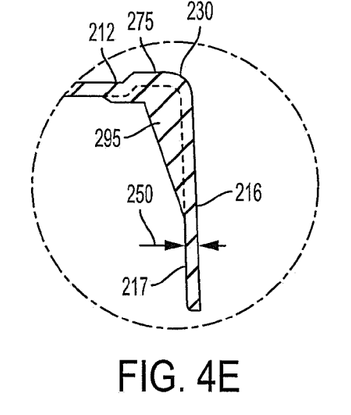
FIG. 4E is a blown-up view of the regions shown as 4E in the cross-sectional view of FIG. 4B.

Rib 295 is shown and described in greater detail in FIG. 4E. In embodiments, the lid 200 has the same number of ribs 295 as lid vents 222. In embodiments, the lid vents 222 and the ribs 295 are co-located around the corner 230 of the lid 200.

Figure 3A:
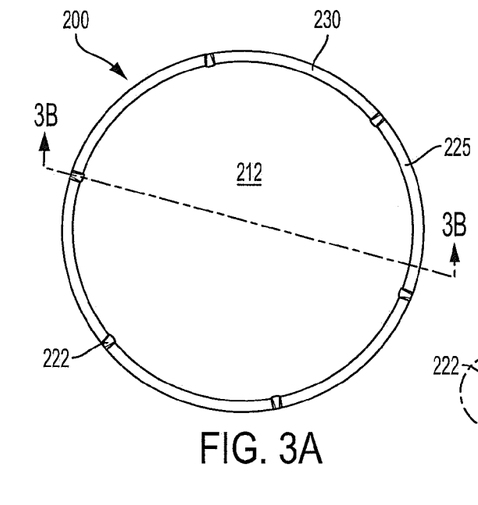
FIG. 3A is a top-down view of the external surface of a lid, according to embodiments.

FIGS. 3A, 3B, 3C and 3D illustrate views of a lid according to an embodiment of the present disclosure. FIG. 3A is a top-down view of the external surface of a lid, according to embodiments. FIG. 3A illustrates the lid 200. The lid is shown with multiple vents 222. In embodiments, the lid has three vents, four vents, five vents or six vents, distributed evenly around the circumference of the lid. As shown in FIG. 3A, the lid has six vents, distributed evenly around the circumference of the lid 200. While the lid embodiment shown in FIG. 3A illustrates the presence of vents, the scope of the disclosure encompasses lids having no vents (not shown).

Figure 3B:
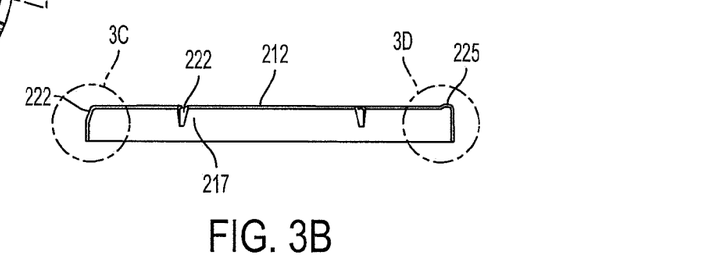
FIG. 3B is a cross-sectional view of a lid, taken at line 3B of FIG. 3A.

FIG. 3B is a cross-sectional view of a lid, taken at line 3B of FIG. 3A. On one side, FIG. 3B illustrates the vent 222 in cross-section, as further illustrated in FIG. 3C. On the other side, FIG. 3B illustrates the corner 230 of the lid 200 in a region that does not contain a vent 222 as further illustrated in FIG. 3D.

Figure 3C:
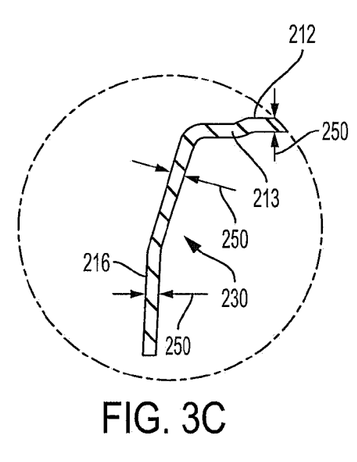
FIG. 3C is a blown-up view of the region shown as 3C in the cross-sectional view of FIG. 3B.

FIG. 3C is a blown-up view of the region shown as 3C in the cross-sectional view of FIG. 3B. FIG. 3C illustrates that the vent 222 is an indentation in the corner 350 of the lid. As described above, the corner 350 defines a lid stacking ring 225, and the vent 222 is present to prevent the lid 200 from sticking to a base or dish stacked on top of the lid 200. FIG. 3C illustrates that, in cross section, the lid thickness 250 at the top circular flat region 212, at the corner 225, at the vent 222 and at the lid sidewall 216 is substantially constant.

Figure 3D:
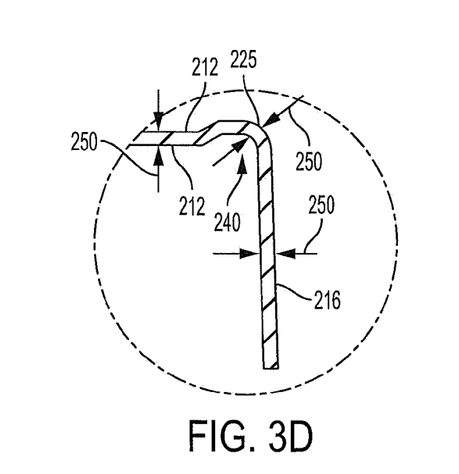
FIG. 3D is a blown-up view of the regions shown as 3D in the cross-sectional view of FIG. 3B.

FIG. 3D is a blown-up view of the region shown as 3D in the cross-sectional view of FIG. 3B, a region that does not contain a vent 222. The lid stacking ring 225 is an annular protrusion around the peripheral edge of the lid 200. Stated another way, the corner of the lid has a protrusion or a bump that forms a lid stacking ring 225 at the corner of the lid 200 of the Petri dish. FIG. 3D illustrates that, in cross section, the lid thickness 250 at the top circular flat region 212, at the corner 225, and at the lid sidewall 216 is substantially uniform. In embodiments, the thickness of the lid at the top circular flat region 212, at the corner 225, and at the lid sidewall 216, are within 30% of each other. That is, in embodiments, the thickness of the sidewall 216, the circular dish region 212 and the corner 226, which has a base stacking ring 225, are not more than 30% different from each other. For example, if the thickness of the sidewall 216 is 4 mm, the thickness of the circular dish region 212 and the lid stacking ring 225 will not vary from 4 mm by more than 30%. That is, the circular lid region 212 will be between and 2.08 and 5.2 mm. In embodiments, the thickness 250 is between 3 mm and 6 mm.

FIGS. 3B, 3C and 3D illustrate that, in cross section, the lid thickness 250 at the top circular flat region 212, at the corner 225, at the vent 222 and at the lid sidewall 216 is substantially constant. Because the thickness 250 is substantially constant, the structure that is the lid stacking ring 230 on the top surface of the lid at the corner 225 forms a groove 240 on the bottom surface of the lid at the corner 225. That is, the inside surface of the lid has an annular groove 240 at the corner. The lid stacking ring 230, which protrudes from the upper surface 212 of the lid 200 at the corner 225, forms a groove 240 on the bottom surface 312 of the lid 200. Because the thickness of the circular lid region 212, the corner 230, and the lid sidewall 216 is substantially constant, the formation of an annular protrusion or lid stacking ring 225 at the corner 230 of the circular lid 225 also forms an annular groove 240 at the interior edge of the circular lid where the sidewall 216 meets the flat circular lid region 212.

FIGS. 4A-4E illustrate views of a lid according to another embodiment of the present disclosure. FIG. 4A is a top-down view of the external surface of a lid, according to embodiments. FIG. 48 is a cross-sectional view of a lid, taken at line 48-C of FIG. 4A. FIG. 4C is a blown-up view of the region shown as 4C in the cross-sectional view of FIG. 48. FIG. 4D is a blown-up view of the regions shown as 4D in the cross-sectional view of FIG. 48. FIG. 4E is a blown-up view of the regions shown as 4E in the cross-sectional view of FIG. 48.

FIG. 4A is a top-down view of the external surface of a lid 200, according to embodiments. As shown in FIG. 4A, an optional gate 290 is present at a location at a corner 230 of the lid 200. In embodiments, the gate 290 is the location at which resin is injected into a mold to create the molded lid. In embodiments, the lid stacking ring 225 located at the corner 230 of the lid 200 is interrupted by a gate 290. In embodiments, the lid has a single gate 290. In additional embodiments, the lid has more than one gate 290. In embodiments, the lid is formed by injection molding, where the resin is injected at a location at a corner of the lid 200. The location of injection molding is a gate 290. Because the thickness of the circular lid region 212, the corner 230, and the lid sidewall 216 is substantially constant, the process of injection molding does not result in the formation of a bubble as the molten resin flows into the mold from a single gate 290, as is more likely when the corner region is thicker than the flat circular lid region or the sidewalls, as discussed above with reference to FIG. 1. The sidewall 216 is usually inclined from a line normal to the top wall 212 (i.e., usually between 90 and 100 degrees rather than precisely at 90 degrees) to facilitate removal of the lid 200 from a mold. The lid stacking ring 225 may extend circumferentially around the lid 200, except for where it is interrupted by the lid gate 290. The lid stacking ring 225 may be concentric with the sidewall 216. The lid stacking ring 225 may define a contact surface upon which the lid 200 rests when the lid 200 is inverted and placed on a surface.

Figure 5A:
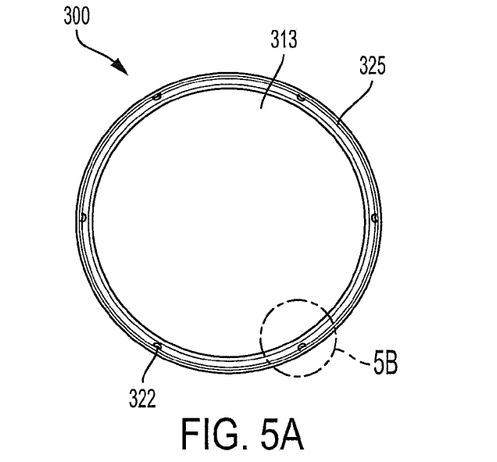
FIG. 5A is a top-down view of the external surface of a dish or base, according to embodiments.

FIGS. 5A-5F illustrate views of a Petri dish or base 300 according to embodiments of the present disclosure. FIG. 5A is a top-down view of the external surface 313 of a dish or base 300, according to embodiments. As shown in FIG. 5A, the base has a circular flat base region 312 having an exterior surface 313 when the base 300 is positioned with the exterior surface 313 of the exterior flat dish region 312 facing up. The dish 300 also has a corner 322 which is a transition between the circular flat base region 312 and the sidewall 316 (shown in FIG. 5B) of the dish 300. Also present at the corner 322 is a base stacking ring 325. The base stacking ring 325 is shown in greater detail in FIGS. 5C and 5D.

Figure 5B:
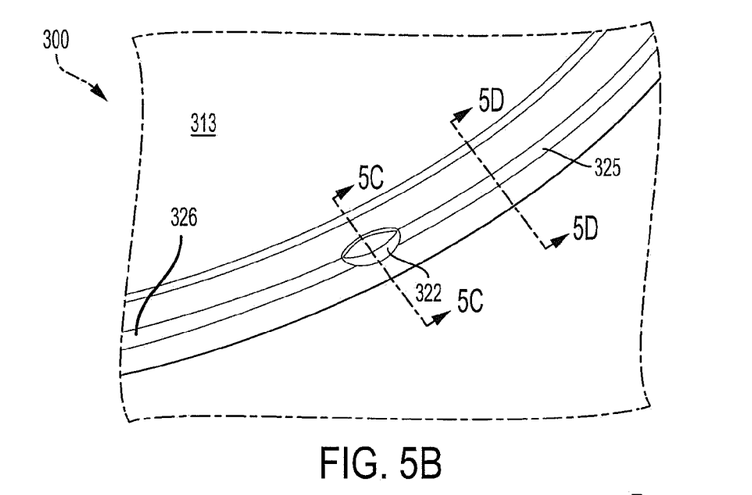
FIG. 5B is a blown up view of the region of the external bottom surface of the dish or base shown in FIG. 5A.

FIG. 5B is a blown up view of the region of the external bottom surface 313 of the dish or base 300 shown as 5B in FIG. 5A. FIG. 5B shows that there is a protrusion at the corner 326 between the circular base region 312 and the sidewall 316 of the base 300. This protrusion is the base stacking ring 325.

FIG. 5B shows that the corner 326, having a base stacking ring 325, may have one or more optional base vents 322. The base vent 322 is a divot or indentation in the base stacking ring 325. The base vent 322, when present, creates a space between the dish 300 and the lid 200 of an adjacent stacked petri dish. This space is shown in more detail in FIG. 7B. The space, created by the base vent 322, allows air to pass between adjacent stacked petri dishes (lids plus bases 100) and prevents the formation of a vacuum between adjacent stacked petri dishes (lid plus base 100). A vacuum formed between adjacent stacked petri dishes 100 creates resistance when removing one Petri dish 100 away from an adjacent stacked Petri dish. This vacuum makes a stack of Petri dishes 100 (such as the stacks shown in FIG. 8 and FIG. 9) difficult to manipulate one at a time. A vacuum formed between adjacent stacked Petri dishes 100 is particularly difficult when the Petri dishes 100 are being manipulated robotically. Robotic handling requires that Petri dishes 100 slide apart from each other when they are stacked. When a vacuum exists between adjacent stacked Petri dishes 100, they do not slide apart from each other as easily.

Figure 5C:
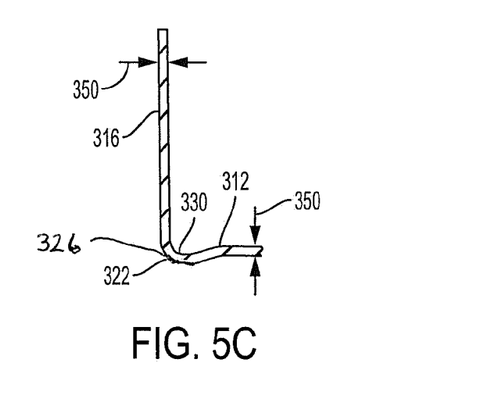
FIG. 5C is a cross-section of the dish shown at line 5C in FIG. 5B.
Figure 5D:
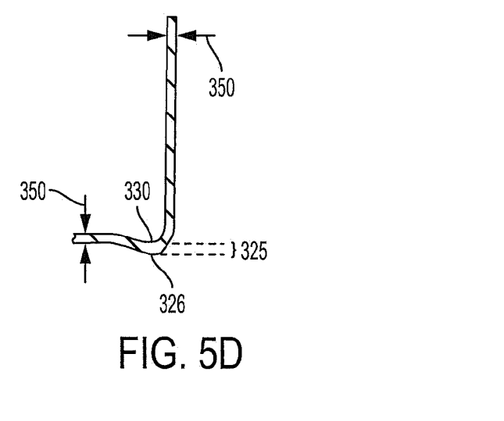
FIG. 5D is a cross section of the dish shown at line 5D in FIG. 5B.

FIG. 5C is a cross-section of the dish shown at line 5C in FIG. 5B. FIG. 5D is a cross-section of the dish shown at line 5D in FIG. 5B. FIG. 5D illustrates that the base has a circular dish region 312, an upwardly extending sidewall 316, and a corner 326 at the intersection of the circular base region and the sidewall 316 of the base 300. At the corner 326 is a protrusion which is the base stacking ring 325. As shown in FIG. 5D, the protrusion extends downwardly. As shown in FIG. 5A, where the base is shown bottom-up, the protrusion extends upwardly. The sidewall 316, the circular dish region 312 and the corner 326 all have a thickness 350. In embodiments, the thickness of the sidewall 316, the circular dish region 312 and the corner 326, which has a base stacking ring 325, are substantially equal. In embodiments, the thickness of the sidewall 316, the circular dish region 312 and the corner 326, which has a base stacking ring 325, are not more than 30% different from each other. For example, if the thickness of the sidewall 316 is 4 mm, the thickness of the circular dish region 312 and the base stacking ring 325 will not vary from 4 mm by more than 30%. That is, the circular dish region 312 will be between and 2.08 and 5.2 mm. In embodiments, the thickness of 350 is between 3 mm and 6 mm. While these thicknesses are provided as examples, the thicknesses of the dishes and lids provided are for example only. Actual thicknesses of the dishes and lids are defined by manufacturing method and may vary.

Because the thickness 350 of the sidewall 316, the circular dish region 312 and the corner 326, which has a base stacking ring 325, are substantially equal, the protrusion that is the base stacking ring 325 extending from the bottom surface 313 of the base 300, forms a channel 330 on the interior surface 311 of the base.

FIG. 5C illustrates the cross-section of the dish 300 shown at line 5C in FIG. 5B. Line 5C in FIG. 5B intersects a base vent 322. The base vent 322 is, in cross-section, a divot or an indentation in the cross-sectional profile of the corner 326 of the base 300. Note, however, that the thickness 350 of the base 300 remains constant from the sidewall 316, through the region of the base vent 322, and across the circular flat base region 312. FIG. 5D illustrates the corner 326 in the absence of a base vent 322. The thickness 350 of the base 300 remains constant from the sidewall 316, through the region of the corner 326, and across the circular flat base region 312. FIG. 5D also illustrates the base stacking ring 325. The base stacking ring 325 is an annular protrusion around the corner of the circular base 300. Because the thickness 350 of the dish 300 is uniform from the sidewall 316, through the corner (which is also the base stacking ring 325) and across the circular flat base region 312, the inclusion of an annular protrusion around the corner 326 of the base 300, on the inside of the base 300, there is a channel 330 around the corner 326 of the base 300. In embodiments, the base 300 has at least three base vents 322. In embodiments, the base has three, four, five, six or more base vents 322. In embodiments the base vents 322 are arranged equidistant from each other around the base stacking ring 325.

Figure 5E:
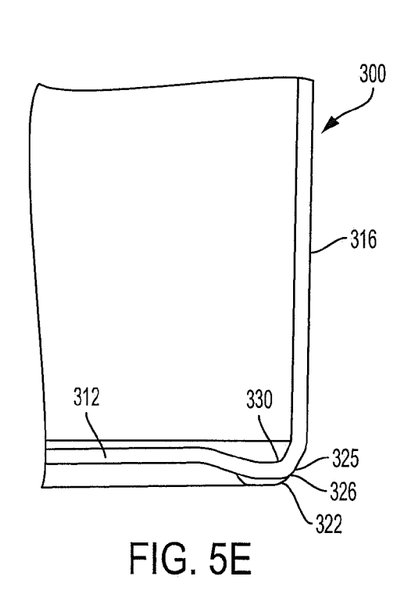
FIG. 5E is an additional cross-section taken at section 5C of FIG. 5B.
Figure 5F:
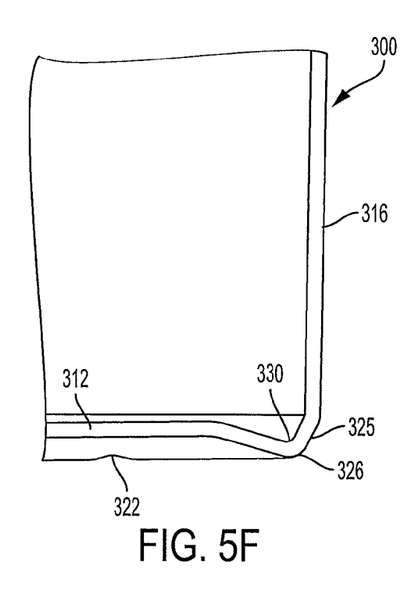
FIG. 5F is an additional cross-section taken at the line shown as 5D of FIG. 5B.

FIG. 5E is an additional cross-sectional view of an embodiment of the base 300 taken at section 5C of FIG. 5B. FIG. 5F is an additional cross-sectional view of an embodiment of the base 300 taken at the line shown as 5D of FIG. 5B. FIG. 5E illustrates the vent 322 in cross section. FIG. 5F illustrates the corner 326, showing the base stacking ring 325, in cross section. Also shown in FIG. 5F, at the back side of the base 300, is a base vent 322. In embodiments, the base 300 has one or more base vents 322. In additional embodiments, the base 300 has 2, 3, 4, 5, 6 or more base vents 322.

The shape (e.g., the base channel 330) between the sidewall 316 and the circular flat base region 312 may facilitate a reduction in bubble formation when agar is introduced into the Petri dish base 300. The base channel 330 may also function to effectively secure the agar in the bottom of the base, thus facilitating better sticking of agar to the base 300. The circular flat base region 312 may be optically flat and optically transparent, which may enhance optical imaging through the circular flat base region 312. In addition, the circular flat base region 212 is flat, to enable agar to sit flat against the base, and also to allow a user to visualize the contents of a petri dish through the bottom of the dish without interference from the material of the flat base region 212.

Figure 6A:
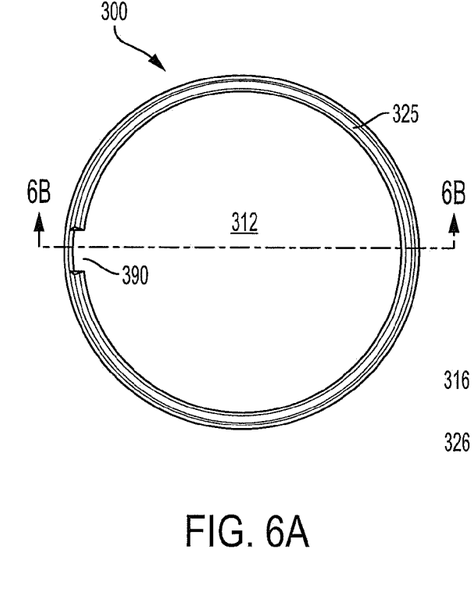
FIG. 6A is a bottom-up view of the external surface of a dish or base, according to embodiments.
Figure 6B:
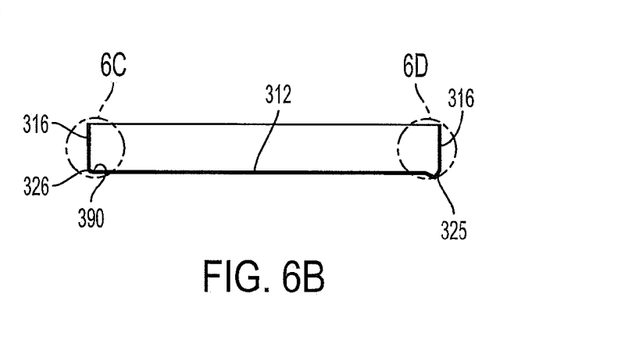
FIG. 6B is a cross-sectional view of the dish or base, taken at line 6B of FIG. 6A.
Figure 6C:
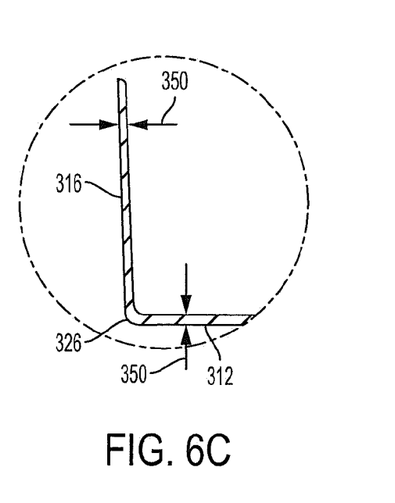
FIG. 6C is a blown-up view of the region shown as 6C in the cross-sectional view of FIG. 6B.
Figure 6D:
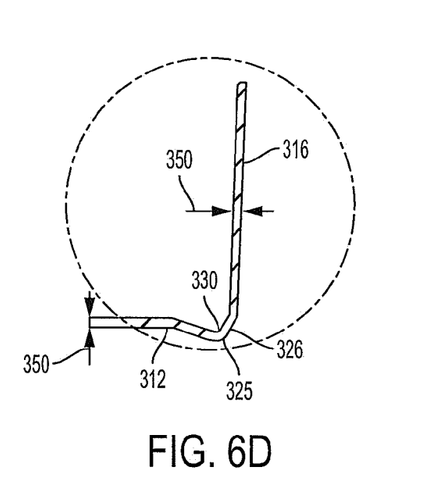
FIG. 6D is a blown-up view of the region shown as 5D in the cross-sectional view of FIG. 6B.

FIGS. 6A-6D illustrate views of a base 300 according to an embodiment of the present disclosure. FIG. 6A is a bottom-up view of the external surface of a base 300, according to embodiments. FIG. 6A illustrates the circular flat region 312 of the base 300, and having a corner 326 having a base stacking ring 325. In the embodiment shown in FIG. 6, there is a gate 390, at least one location along the corner 326 of the base 300. The gate 390 is the location of injection of liquid plastic material into the mold in an injection molding process. That is, the gate 390 is an artifact of injection molding. FIG. 6B is a cross-sectional view of the base 300, taken at line 6B of FIG. 6A. FIG. 6C is a blown-up view of the region shown as 6C in the cross-sectional view of FIG. 6B. As shown in FIG. 6C, at the location of the gate, the corner 326 is square. That is, at the location of the gate 390, there is no base stacking ring. Or, in embodiments, the base stacking ring 325 located at the corner 326 of the base 300 is interrupted by a gate 390. Note however, that the thickness 350 of the part is uniform from the sidewall 316, through the corner 326 and across the circular flat region 312, in the presence or absence of a gate 390. FIG. 6D is a blown-up view of the region shown as 5D in the cross-sectional view of FIG. 6B. In the cross-sectional view of FIG. 6D that crosses through the base stacking ring 325, the channel 330 on the inside surface of the corner 326 is shown. The thickness 350 of the part is uniform from the sidewall 316, through the corner 326 which comprises a base stacking ring 325, and across the circular flat region 312. The base stacking ring 325 may be concentric with the sidewall 316. The base stacking ring 325 may define a contact surface upon which the base 300 rests when the base 300 is placed on a surface.

Figure 7A:
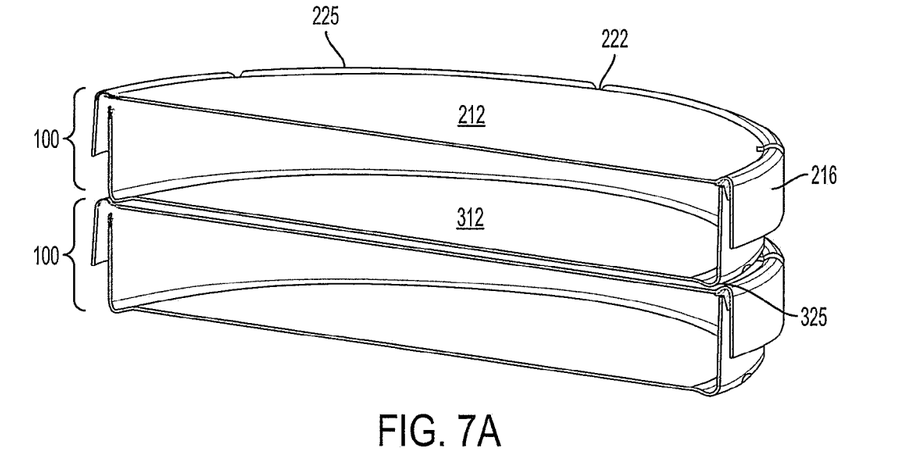
FIG. 7A is a cut-away side view of two stacked Petri dishes with lids.
Figure 7B:
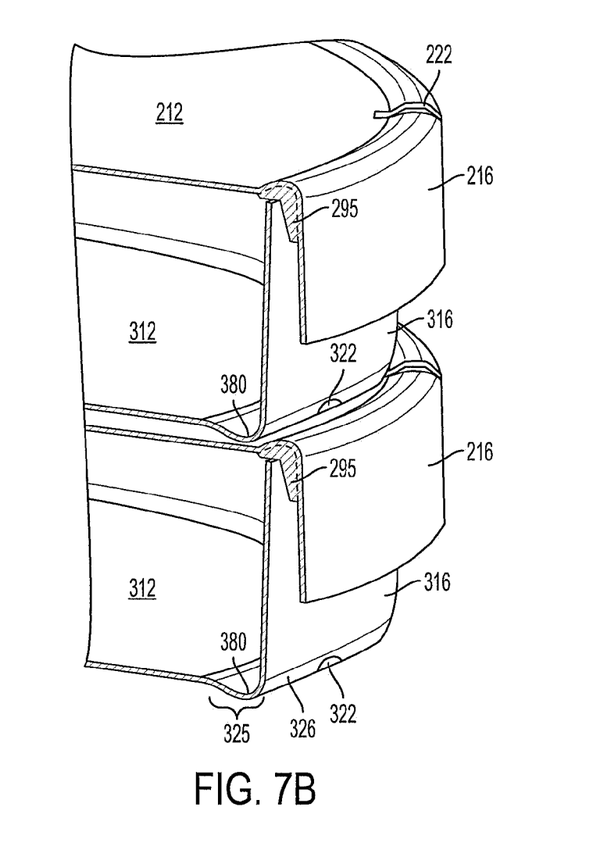
FIG. 7B is a blown-up illustration of the region shown as 7B in FIG. 7A.

FIGS. 7A and 7B illustrate stacked Petri dishes 100, which include a dish 300 and a lid 200. FIG. 7A is a cut-away side view of two stacked Petri dishes 100. FIG. 7B is a blown-up illustration of the region shown as 7B in FIG. 7A. FIG. 7A illustrates that, when stacked, the base stacking ring 325 fits inside the lid stacking ring 225. Lid vents 222 create an air pathway between the lid 200 of the lower stacked Petri dish 100 and the base 300 of the upper Petri dish 100. Base vent 322 also provides a space between the base 300 of the upper Petri dish 100 and the lid 200 of the lower Petri dish 100. As shown in FIG. 7B, the lid 200 sits atop the base 300, and is held above the base 300 by means of the rib 295. The lid 200 may comprise one, two, three, four, five or more lid ribs 295, for example six equally spaced lid ribs 295 (i.e., separated by approximately 60 degrees).

Figure 8:
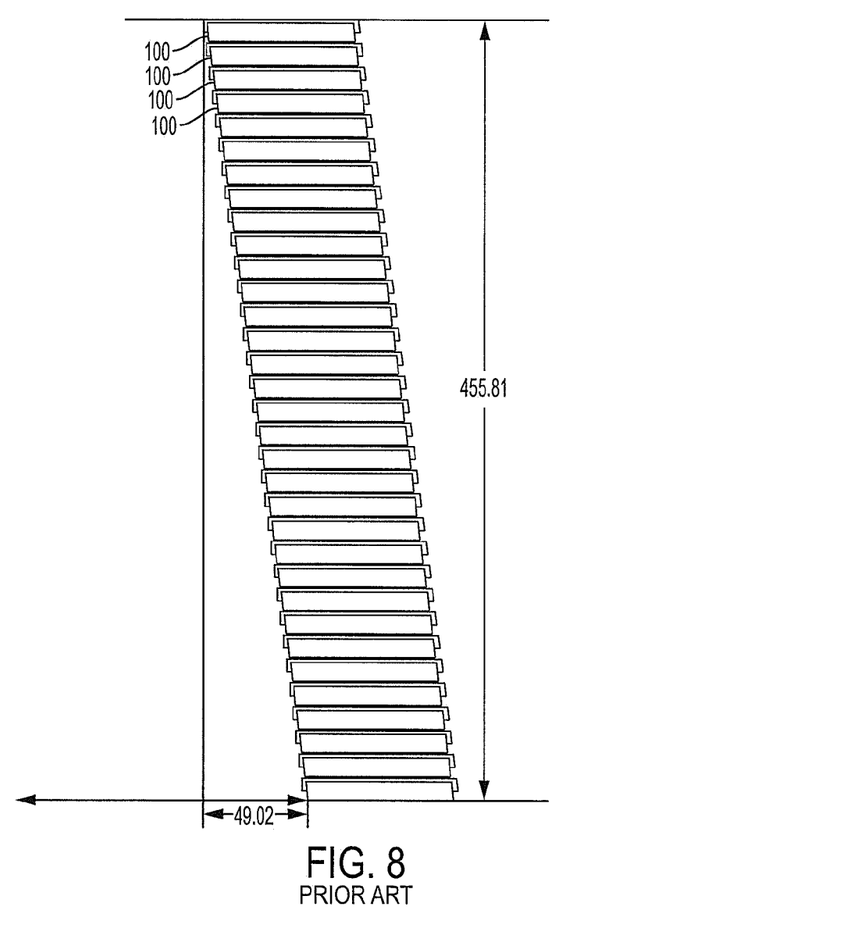
FIG. 8 is an illustration of a stack of 33 prior art Petri dishes with lids.

FIG. 8 is an illustration of a stack of 33 prior art Petri dishes with lids 100. As shown in FIG. 8, a stack of 33 prior art Petri dishes 100 can form a "lean" (/distance from the base to the top corner of the stack (49.02 cm)/height of the stack of Petri dishes (455.81 cm)) of approximately 10% (49.02 cm/455.81 cm=0.1075.)

Figure 9:
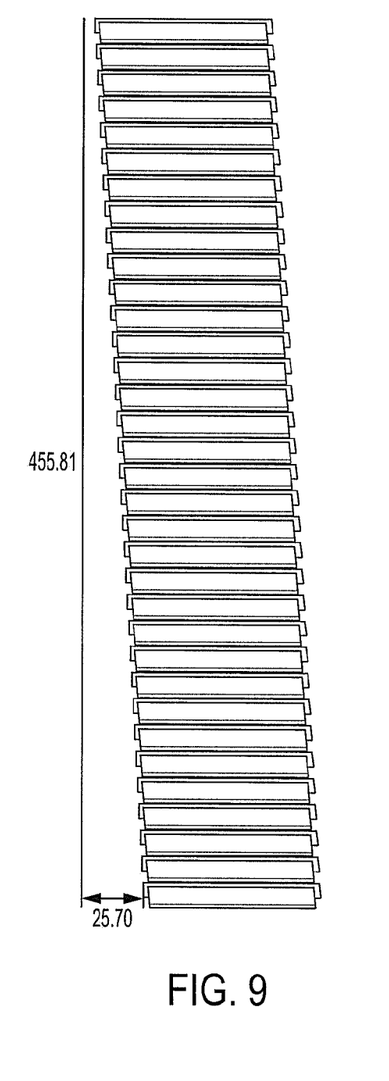
FIG. 9 is an illustration of a stack of 33 Petri dishes with lids, according to an embodiment.

FIG. 9 is an illustration of a stack of 33 Petri dishes with lids, according to an embodiment of the present disclosure. In contrast to the stack illustrated in FIG. 8, Petri dishes 100 having the lid stacking rings 225 and base stacking rings 325 as illustrated in FIGS. 2-7 exhibit reduced "lean" (distance 25.70 cm/height 455.81 cm 25.7=0.0563) of approximately 5%.

The measurements shown in FIG. 8 and FIG. 9 are for example only. Actual measurements depend on the size of the Petri dishes, the height of the sidewalls of the bases of the Petri dishes. FIG. 8 and FIG. 9 are provided to illustrate the effect of the use of triangular ribs to center a lid on a base, combined with the presence of a lid stacking ring and a base stacking ring. The lid stacking ring and the base stacking ring allow the base of a top Petri dish to sit within the lid stacking ring of the lower adjacent Petri dish. These features, alone or in combination, provide Petri dishes which stack in a straighter stack compared to other Petri dishes.

According to an aspect of the present disclosure, the stackable, thin-walled lid 200 and base 300 may be made using various plastic forming technologies, including injection molding and thermoforming. With injection molding, parts are formed by injecting material into a mold. Injection molding typically uses a ram or screw-type plunger to force molten plastic material into a mold cavity. The material then solidifies into a shape that has conformed to the contour of the mold. Injection molding may be used to process both thermoplastic and thermosetting polymers. Thermoforming is a manufacturing process where a plastic sheet is heated to a pliable forming temperature, formed to a specific shape in a mold, and trimmed to create a usable product. Compared to injection molding, thermoforming has the potential to have an overall lower manufacturing cost. A thermoformed part can be thinner than an injection molded part because the thermoformed part does not require that liquid polymeric material be injected into a mold. Thinner parts require less raw material, less polymeric material.

Different advantages may be achieved depending on the method of manufacture. During injection molding, for example, because the cross-section of the mold is constant, the rate of material fill into the mold may be constant and homogeneous. This may minimize or eliminate the capture of air bubbles and the formation of flow lines in the finished lid 200 and base 300. Alternatively, a lid 200 and base 300 made via thermoforming may exhibit no retained internal stress, no marks due to the injection valve gate, and no flow lines.

The lid 200 and base 300 may be formed from a thermoplastic or thermosetting polymer including reground or recycled resins such as polystyrene (PS), acrylonitrile butadiene styrene, polycarbonate (PC), polyethylene (PE), polyethylene terephthalate (PET), polymethyl methacrylate (PMMA), polypropylene, cyclic olefin co-polymers (COCs), transparent co-polymers such as styrene maleic anhydride, poly(styrene-butadiene-styrene) (SBS), as well as combinations thereof. The thermoplastic or thermosetting polymer may be optically transparent.

In embodiments, the Petri lid 200 and base 300 may be manufactured by injection molding, which involves injecting liquid plastic material into a mold, and allowing the liquid plastic material to cool before removing the formed part from the mold. In embodiments, the petri lid or base may be manufactured by vacuum forming or thermoforming, which involves providing a sheet of plastic material, heating the sheet to a pliable forming temperature, and thermoforming in a mold the sheet into a component of a Petri dish having a substantially constant cross-sectional thickness.

According to an aspect of the present disclosure, a Petri dish lid 200 or a Petri dish base 300, or both, may have the described features. The Petri dish lid 200 may have a constant wall thickness. Similarly, the Petri dish base 300 may have a constant wall thickness. The thin-walled lid 200 and base 300 may be stackable and require 15 to 20% less resin to produce than prior art Petri dishes. Moreover, the present disclosure addresses a number of constraints associated with thin-walled parts. Namely, manufacturing concerns incumbent to thin-walled designs include increased residual stresses in the resin, and variable melt flow fronts that cause defects such as trapped air, and weld lines that make the parts susceptible to cracking.

A lid 200 and a base 300 of the Petri dish 100 may be formed via the same or different manufacturing methods and using the same or different materials. For instance, the lid 200 and base 300 may each be formed by thermoforming. For instance, the lid 200 and base 300 may each comprise PS. Optionally, a cushioning effect may be provided between the lid 200 and the base 300 by controlling the relative stiffness of each component via materials selection, which can minimize breakage even for thinner designs. For instance, the lid 200 may comprise a relatively compliant material such as PET or PS-SBS while the base 300 may comprise a less compliant material such as PS. Optionally, one or both of the lid 200 and the base 300 may be optically transparent.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a Petri dish comprising a base and a lid include embodiments where a Petri dish consists of a base and a lid and embodiments where a Petri dish consists essentially of a base and a lid.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the claims.

The invention claimed is:

1. A dish comprising:
a polymeric base having a circular dish region, a corner, and an upwardly extending sidewall, the polymeric base comprising:
a channel in an interior surface of the base at the corner, and
a base stacking ring in an exterior surface of the base at the corner;
a polymeric lid having a circular flat lid region, a corner, and a downwardly extending sidewall, the polymeric lid comprising:
a groove in an interior surface of the lid at the corner; and
a lid stacking ring that is a raised ring of material in an exterior surface of the lid at the corner, the lid stacking ring circumscribing and bordering the circular flat lid region; and a plurality of lid vents in the lid, the lid vents comprising an indentation in and extending from the downwardly extending sidewall, through the corner of the lid, and to the circular flat lid region, wherein each of the circular dish region, the upwardly extending sidewall and the corner have a thickness, the thicknesses of the circular dish region, the upwardly extending sidewall and the corner being within 30% of each other, wherein each of the circular flat lid region, the downwardly extending sidewall and the corner have a thickness, the thicknesses of the circular flat lid region, the downwardly extending sidewall and the corner being within 30% of each other, and wherein, when the polymeric base is stacked on top of the polymeric lid, the base stacking ring fits concentrically inside the lid stacking ring and is disposed on the circular flat lid region.

2. The dish of claim 1 further comprising at least three base vents in the base stacking ring.

3. The dish of claim 2 comprising at least 4 base vents in the base stacking ring.

4. The dish of claim 2 wherein the base vents are arranged equidistant from each other.

5. The dish of claim 1, wherein the base stacking ring is interrupted by a gate.

6. The dish of claim 1 wherein the lid further comprises at least three ribs extending downwardly from the interior surface of the lid, at the corner.

7. The dish of claim 6 wherein the ribs are triangular.

8. The dish of claim 6 wherein the ribs are equidistant from each other.

9. The dish of claim 8, wherein the plurality of lid vents comprises at least three lid vents, and wherein the ribs and the lid vents are co-located in the lid.

10. The dish of claim 1, wherein the plurality of lid vents comprises at least three lid vents.

11. The dish of claim 10 wherein the lid vents are equidistant from each other.

12. The dish of claim 1, wherein the lid stacking ring is interrupted by a gate.

\* \* \* \* \*